US012760054B2

(12) United States Patent
Li et al.

(10) Patent No.: US 12,760,054 B2
(45) Date of Patent: Oct. 13, 2026

(54) METHOD FOR PURIFYING SUCRALOSE

(71) Applicant: ANHUI JINHE INDUSTRIAL CO., LTD., Chuzhou (CN)

(72) Inventors: Zhenghua Li, Chuzhou (CN); Jiaxin Xia, Chuzhou (CN); Chuanjiu Xu, Chuzhou (CN); Guojia Xu, Chuzhou (CN)

(73) Assignee: ANHUI JINHE INDUSTRIAL CO., LTD., Chuzhou (CN)

( * ) Notice: Subject to any disclaimer, the term of this patent is extended or adjusted under 35 U.S.C. 154(b) by 603 days.

(21) Appl. No.: 18/250,728

(22) PCT Filed: Nov. 13, 2020

(86) PCT No.: PCT/CN2020/128654
§ 371 (c)(1),
(2) Date: Apr. 26, 2023

(87) PCT Pub. No.: WO2022/099606
PCT Pub. Date: May 19, 2022

(65) Prior Publication Data
US 2023/0399351 A1 Dec. 14, 2023

(51) Int. Cl.
*C07H 5/02* (2006.01)
*B01D 9/00* (2006.01)

(52) U.S. Cl.
CPC ............. *C07H 5/02* (2013.01); *B01D 9/0031* (2013.01)

(58) Field of Classification Search
CPC .................................... C07H 5/02; C07H 1/06
See application file for complete search history.

(56) References Cited

U.S. PATENT DOCUMENTS

| | | | | |
|---|---|---|---|---|
| 5,498,709 A | 3/1996 | Navia et al. | | |
| 2003/0171575 A1* | 9/2003 | Catani | C07H 5/02 | 536/119 |

FOREIGN PATENT DOCUMENTS

| | | | | |
|---|---|---|---|---|
| CN | 101177437 A | * | 5/2008 | C07H 5/02 |
| CN | 101768193 A | | 7/2010 | |
| CN | 102336786 A | * | 2/2012 | C07H 5/02 |
| CN | 102391319 A | | 3/2012 | |
| CN | 106188166 A | | 12/2016 | |
| CN | 106674292 A | | 5/2017 | |
| CN | 109503680 A | | 3/2019 | |

OTHER PUBLICATIONS

EPO English machine translation of CN 101177437 A, published May 14, 2008, [https://worldwide.espacenet.com/], accessed online on Sep. 23, 2025. (Year: 2008).*
EPO English machine translation of CN 102336786 A, published Feb. 1, 2012, [https://worldwide.espacenet.com/], accessed online on Dec. 15, 2025. (Year: 2012).*
Cheng, Chen et al., "Analysis on the Production and Application of Sucrose Trichlorose" Industry Review, 2019.
Office Action for CN 202080004013.X issued Mar. 17, 2022.
Office Action for CN 202080004013.X issued Aug. 12, 2022.
International Search Report for PCT/CN2020/128654 dated Jul. 27, 2021.

* cited by examiner

*Primary Examiner* — Jonathan S Lau
(74) *Attorney, Agent, or Firm* — Knobbe, Martens, Olson & Bear LLP

(57) ABSTRACT

Disclosed is a method for purifying sucralose, including: removing a solvent from a sucralose reaction solution to obtain a concentrated crude sucralose solution; under stirring, adding ethyl acetate into the concentrated crude sucralose solution, heating to a preset temperature, and holding at the preset temperature for a first preset time to obtain a crude product slurry with a certain amount of a sucralose crystal; and subjecting the crude product slurry to gradient cooling to an endpoint temperature, holding at the endpoint temperature for a second preset time, and filtering to obtain a sucralose crystal.

7 Claims, 3 Drawing Sheets

METHOD FOR PURIFYING SUCRALOSE

CROSS REFERENCE TO RELATED APPLICATION

This application is a U.S. National Phase Application of PCT International Application Number PCT/CN2020/128654, filed on Nov. 13, 2020, designating the United States of America and published in the Chinese language. The disclosures of the above-referenced application are hereby expressly incorporated by reference in its entirety.

TECHNICAL FIELD

The present disclosure belongs to the field of manufacturing fine chemical products, and specifically relates to a method for purifying sucralose.

BACKGROUND ART

Sucralose is a new sweetener with advantages such as high sweetness, no calories, high stability, and high safety, and has very promising market prospects. Regarding the synthesis process of sucralose, great progress has been made since the advent of sucralose. So far, the mainstream synthesis process of sucralose is a monogroup-protected synthesis method (as shown in FIG. 1), in which the 6-hydroxyl with the highest activity in sucrose is selectively protected usually in the form of acetate to obtain sucrose-6-acetate, the 4-hydroxyl, 1'-hydroxyl, and 6'-hydroxyl of sucrose-6-acetate are selectively subjected to a chlorination reaction to obtain sucralose-6-acetate, and sucralose-6-acetate is then subjected to remove the acetyl protecting group to finally obtain sucralose.

At present, the improvement on the process for producing sucralose mainly focuses on the improving the multi-step synthesis process, while the improvement on the process for purifying sucralose is little reported. The process for purifying sucralose in the prior art is mainly conducted by extracting an aqueous solution of crude sucralose with a large amount of butyl acetate as an extraction solvent, which has the disadvantage of large solvent consumption resulting in a large amount of organic waste liquid. In addition, due to the high boiling point of butyl acetate, the subsequent removal process involves high energy consumption, and the use of butyl acetate increases the types of materials to be handled in the process. These increase the production costs and are not conducive to clean production. Therefore, there is still much room for improvement of the process for purifying sucralose.

SUMMARY

In view of the above problems that the process for purifying sucralose in which impurities are extracted with butyl acetate in the prior art has disadvantages such as complicated operations, large solvent consumption, and high energy consumption and additional treatment costs for solvent removal, a method for purifying sucralose is provided in the present disclosure to overcome or at least partially solve the above problems.

According to a first aspect of the present disclosure, there is provided a method for purifying sucralose, including:

concentration: removing a solvent from a sucralose reaction solution to obtain a concentrated crude sucralose solution;

slurrying: under stirring, adding ethyl acetate into the concentrated crude sucralose solution, heating to a preset temperature, and holding at the preset temperature for a first preset time to obtain a crude product slurry containing a certain amount of a sucralose crystal; and collection: under stirring, subjecting the crude product slurry to gradient cooling to an endpoint temperature, and holding at the endpoint temperature for a second preset time to obtain a sucralose crystal.

According to a second aspect of the present disclosure, there is provided sucralose prepared by the method described above, wherein the sucralose has a high performance liquid chromatography (HPLC) purity of higher than or equal to 97%.

The present disclosure has the following beneficial effects:

Compared with the impurity extraction process using butyl acetate widely used in the prior art, a method for purifying sucralose is provided in the present disclosure, in which a concentrate of crude sucralose is directly slurried without redissolving crude sucralose in a solution. The method for purifying sucralose of the present disclosure has the advantages of simple operations, small treatment capacity, and small solvent consumption. In addition, because ethyl acetate is a solvent widely used in the process for producing sucralose (such as chlorination), the use of ethyl acetate will not increase the additional species in the process, and a boiling point of ethyl acetate is much lower than that of butyl acetate, such that the energy consumption in the distillation for solvent recovery is greatly reduced, which is conducive to improving the production efficiency and reducing the production costs.

The above description is merely a summary of the technical solutions of the present disclosure. In order to allow the technical means of the present disclosure to be understood clearly and implemented in accordance with the specification and allow the above and other objects, features, and advantages of the present disclosure to be obvious and easy to understand, specific embodiments of the present disclosure are described below.

BRIEF DESCRIPTION OF THE DRAWINGS

By reading the detailed description of the following preferred embodiments, various other advantages and benefits will become apparent to those of ordinary skill in the art. The accompanying drawings are provided merely to illustrate the preferred embodiments, rather than to limit the present disclosure. Throughout the accompanying drawings, the same reference numerals represent the same components. In the accompanying drawings.

DETAILED DESCRIPTION OF THE EMBODIMENTS

Exemplary embodiments of the present disclosure will be described in detail below with reference to the accompanying drawings. Although the accompanying drawings show exemplary embodiments of the present disclosure, it should be understood that the present disclosure may be implemented in various forms and should not be limited to the embodiments set forth herein. Instead, these embodiments are provided to make the present disclosure thoroughly understood and make a scope of the present disclosure fully conveyed to those skilled in the art.

The inventive concept of the present disclosure is as follows:

Due to the high polarity of sucralose, the solubility of sucralose in water is much higher than the solubility of sucralose in ethyl acetate, while the impurities in crude sucralose obtained after a deacetyl reaction are mostly species with low polarity; it has been found through studies in the present disclosure that the slurrying of crude sucralose with ethyl acetate could selectively remove a variety of impurities, thus achieving an excellent purification effect.

Figure 1:
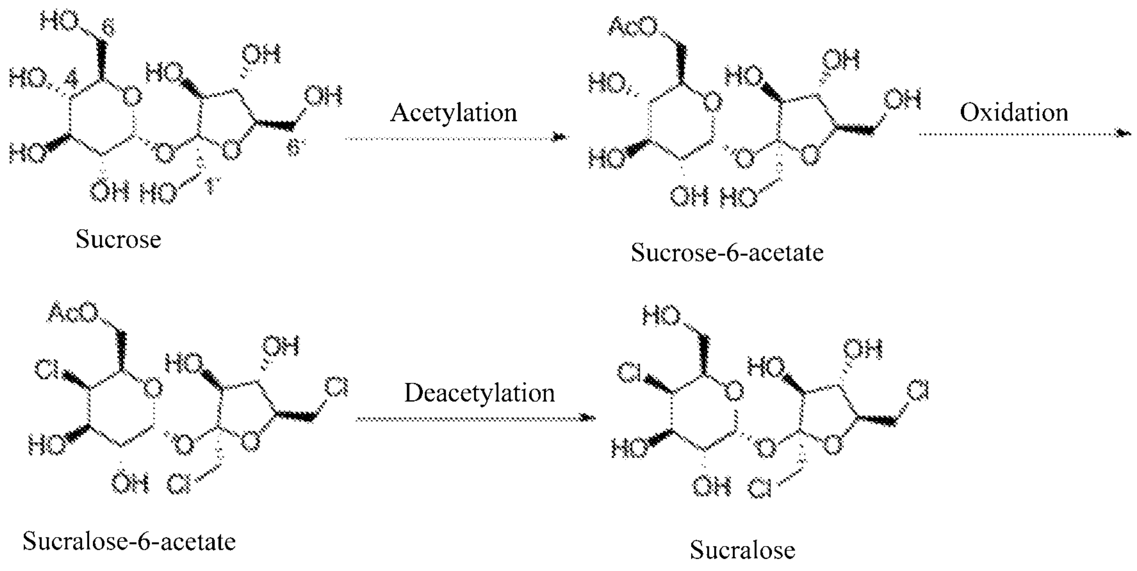
FIG. 1 shows a schematic diagram illustrating a process flow of the monogroup-protected synthesis method for sucralose in the prior art.
Figure 2:
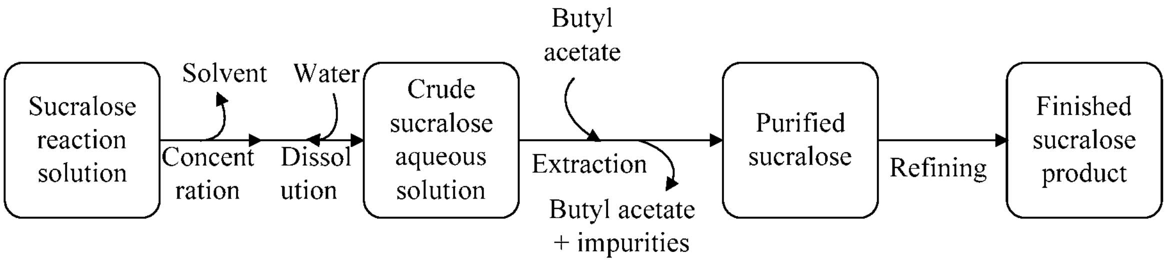
FIG. 2 shows a schematic diagram illustrating a process flow for extracting sucralose with butyl acetate in the prior art.

FIG. 2 shows a schematic diagram illustrating a process flow for extracting sucralose with butyl acetate in the prior art. As shown in FIG. 2, a deacetyl reaction solution containing crude sucralose is first concentrated to remove a solvent, then water is added for dissolution to obtain an aqueous solution of crude sucralose, then the aqueous solution is subjected to extraction with butyl acetate to remove impurities, and then the impurity-removed aqueous solution is refined by a method such as crystallization to obtain purified sucralose. Due to the use of butyl acetate with a high boiling point, the above method has defects such as large solvent consumption, high energy consumption, and increased raw material species used in the process.

Figure 3:
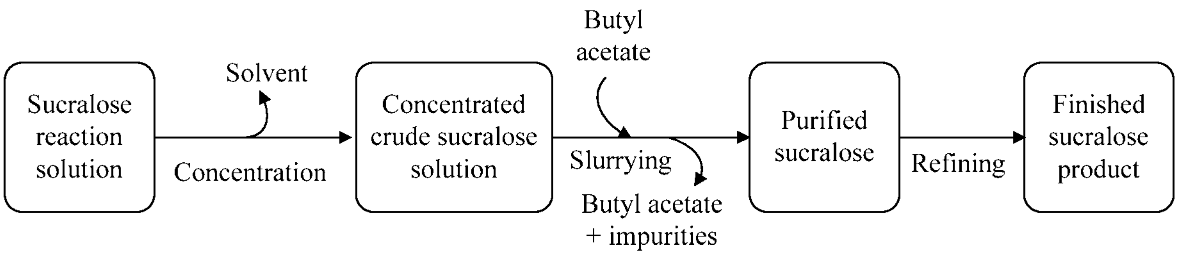
FIG. 3 shows a schematic diagram illustrating a process flow of a method for purifying sucralose according to an embodiment of the present disclosure.

FIG. 3 shows a schematic diagram illustrating a process flow of a method for purifying sucralose according to an embodiment of the present disclosure, and the method for purifying sucralose includes:

- concentration: a solvent is removed from a sucralose reaction solution to obtain a concentrated crude sucralose solution.

The method for purifying sucralose provided in the present disclosure is conducted for a crude sucralose-containing mixed solution produced after a deacetyl reaction of sucralose-6-acetate during the preparation of sucralose, and is intended to purify sucralose in the crude sucralose-containing mixed solution through a certain technical means. In the present disclosure, the crude sucralose-containing mixed solution is called a sucralose reaction solution.

In the method for purifying sucralose provided by the present disclosure, a large amount of organic solvent in the sucralose reaction solution is first removed by a conventional means in the prior art to obtain a crude sucralose-containing concentrated solution, which is called a concentrated crude sucralose solution. In some embodiments of the present disclosure, vacuum distillation or atmospheric distillation is used to remove the organic solvent.

Slurrying: under stirring, ethyl acetate is added to the concentrated crude sucralose solution, and a resulting mixture is heated to a preset temperature, and held at the preset temperature for a first preset time to obtain a crude product slurry containing a certain amount of a sucralose crystal.

As shown in FIG. 2, in the prior art, after a solvent is removed from the sucralose reaction solution, a large amount of water is usually used to dissolve the sucralose reaction solution after removing the solvent to obtain a crude sucralose-containing aqueous solution; then butyl acetate is added for extraction, such that impurities are extracted into butyl acetate due to different polarities of substances in the reaction solution; and after the extraction is completed, the resulting aqueous solution is subjected to crystallization by concentration to obtain a sucralose crystal.

In the present disclosure, instead of dissolving the sucralose reaction solution obtained after removing the solvent in a large amount of water, ethyl acetate is directly added to the concentrated crude sucralose solution, and the concentrated crude sucralose solution is slurried under preset conditions. In this process, a variety of organic impurities with small polarity in the sucralose reaction solution will enter into ethyl acetate, and subsequently, an ethyl acetate mother liquor containing impurities is removed through filtration, thereby removing the impurities in the sucralose reaction solution.

During the slurrying process, the sucralose crystal is mostly precipitated in the slurry. During the slurrying of the present disclosure, since the dissolution of the sucralose reaction solution obtained after removing the solvent using a large amount of water is not required, the wastewater production and energy consumption are significantly reduced while the process flow is simplified.

Collection: under stirring, the crude sucralose slurry is subjected to gradient cooling to an endpoint temperature, and held at the endpoint temperature for a second preset time to obtain a sucralose crystal.

The collection is conducted to promote the complete precipitation of the sucralose crystal by cooling. After the slurrying is completed, it is not necessary to separate ethyl acetate from the sucralose reaction solution, but the crude product slurry containing a certain amount of a sucralose crystal is directly subjected to gradient cooling, such that sucralose unprecipitated in the reaction solution is crystallized and precipitated. Specifically, under stirring, the crude sucralose slurry is subjected to gradient cooling to an endpoint temperature, held at the endpoint temperature for a second preset time, and filtered to obtain the sucralose crystal.

In some embodiments of the present disclosure, the method for purifying sucralose may further include refining: further refining the obtained sucralose to obtain a refined sucralose crystal.

In order to obtain a sucralose crystal with improved purity, the obtained sucralose may be further refined. In some embodiments of the present disclosure, the obtained sucralose is subjected to recrystallization to obtain sucralose with improved purity.

In this embodiment, a method for recrystallizing sucralose is recommended, including:

- dissolution: adding sucralose into deionized water, heating the sucralose for dissolution to obtain a sucralose solution, decolorizing the sucralose solution with activated carbon, and filtering the sucralose solution to obtain a recrystallization solution;
- concentration: concentrating the recrystallization solution to by evaporation to obtain a concentrated recrystallization solution with a preset concentration;
- nucleation: leaving the concentrated recrystallization solution to stand at a preset temperature for a period of time to produce a sucralose crystal nucleus in the concentrated recrystallization solution;
- crystallization: subjecting the concentrated recrystallization solution containing the sucralose crystal nucleus to gradient cooling to obtain a recrystallization solution containing a large amount of a sucralose crystal; and filtration: centrifuging the recrystallization solution containing a large amount of a sucralose crystal to obtain a solid, and water-washing and drying the solid to obtain the sucralose crystal.

Amount of Ethyl Acetate

In the present disclosure, there is no limitation on the amount of ethyl acetate. In some embodiments, ethyl acetate is added in a volume of 0.2 mL to 0.5 mL per gram of the concentrated crude sucralose solution. If the volume of ethyl acetate is less than 0.2 mL/1 gram of the crude sucralose solution, indicating an under-use of ethyl acetate, the organic impurities in the sucralose reaction solution could not be completely extracted. If the volume of ethyl acetate is more than 0.5 mL/1 gram of the crude sucralose solution, indicating an over-use of ethyl acetate, ethyl acetate is unnecessarily wasted, and the crude sucralose slurry has an excessively low concentration, which is not conducive to the subsequent crystallization of sucralose, and may even cause problems such as incomplete sucralose crystallization, complicated and diversified crystal forms, and low yield.

Preset Temperature in the Slurrying

In the present disclosure, there is no limitation on the preset temperature in the slurrying. In some embodiments, the preset temperature is in a range of 45° C. to 65° C. If the preset temperature is lower than 45° C., indicating an over-low temperature, the ethyl acetate could not be well mixed with the concentrated crude sucralose solution. If the preset temperature is higher than 65° C., indicating an over-high temperature, it is easy to cause local overheating of the concentrated crude sucralose solution or even boiling, and invalid volatilization of ethyl acetate.

First Preset Time in the Slurrying

In the present disclosure, there is no limitation on the first preset time (namely, slurrying time) in the slurrying. In some embodiments, the first preset time is in a range of 0.5 h to 3 h. If the first preset time is less than 0.5 h, which indicates an over-short time for slurrying (namely, extraction), a variety of organic impurities could not completely enter the ethyl acetate. If the first preset time is more than 3 h, indicating an over-long time for slurrying (namely, extraction), the overall purification process takes an over-long time without any additional beneficial effects.

Gradient Cooling

In the present disclosure, the gradient cooling in the collection is conducted to facilitate the rapid and massive precipitation of the unprecipitated sucralose crystal. In the present disclosure, there is no limitation on the gradient cooling in the collection. In some embodiments, the gradient cooling is conducted by cooling the crude product slurry to an endpoint temperature at a cooling rate of 1° C./10 min to 3° C./10 min; and the endpoint temperature is in a range of 0° C. to 10° C.

The gradient cooling of the crude sucralose slurry could allow the massive precipitation of the sucralose crystal. In some embodiments, the gradient cooling is conducted by cooling the crude sucralose slurry from the preset temperature in the slurrying to a temperature of 0° C. to 10° C. at a cooling rate of 1° C./10 min to 3° C./10 min. During the cooling process, the crystal grows rapidly in a large quantity, and at the end of the cooling (namely, when the endpoint temperature is reached), most of the sucralose in the solution is crystallized and precipitated.

In the crystallization, after the crude sucralose slurry is cooled to the endpoint temperature through gradient cooling, the crude sucralose slurry is held at the endpoint temperature for a second preset time. In the present disclosure, there is no limitation on the second preset time. In some embodiments, the second preset time is in a range of 0.5 h to 3 h. If the second preset time is less than 0.5 h, indicating an over-short time for crystallization, the crystallization could not be conducted thoroughly, and a part of sucralose still remains in the crude sucralose slurry. If the second preset time is more than 3 h, indicating an over-long time for crystallization, a resulting sucralose crystal has an irregular and complicated crystal form.

Compared with the existing process for purifying sucralose through impurity extraction with butyl acetate, the present disclosure has the following advantages:

1. The method of the present disclosure involves simple operations, small treatment capacity, and small solvent consumption. 2. The ethyl acetate used could be directly recycled for a production system of sucralose, and will not increase the types of materials to be handled in the entire process. 3. Ethyl acetate has a low boiling point, which makes it possible to greatly reduce the energy consumption in the distillation for solvent removal. 4. The prepared sucralose has a high purity, could be easily further purified and refined, and has an HPLC purity of 97% or more.

Drug Sources or Test Methods Involved in the Present Disclosure:

The test methods used in examples and comparative examples of the present disclosure are described below, and will not be repeated in each example.

Source of the Sucralose Reaction Solution

In some embodiments of the present disclosure, the crude sucralose (namely, the sucralose reaction solution) may be a commercially-available finished product or produced by any method in the prior art, including, but not limited to, monogroup-protected synthesis method, multigroup-protected synthesis method, and an enzymatic catalysis method, which is not limited in the present disclosure.

Other Drugs

In some embodiments of the present disclosure, drugs such as ethyl acetate, distilled water, and standard substances are required, and may be commercially available. The distilled water may also be laboratory distilled water, which is not limited in the present disclosure.

Analysis and Determination Conditions of Sucralose Purity

A test method for sucralose purity analysis involved in the present disclosure could refer to the Chinese National Standard "GB 25531-2010 for Food Additive Sucralose".

A high performance liquid chromatograph from Shimadzu, Japan: RID-10A differential refractive index detector, LC-10ADVP high-pressure pump, and CTO-incubator; chromatographic column: Agilent XDB C18 column (250 mm×4.6 mm, 5 μm); mobile phase: methanol-0.125% dipotassium phosphate (DKP) aqueous solution (4:6); column temperature: 30° C.; and flow rate: 1.0 mL/min. Methanol (chromatographically pure), DKP (analytically pure), ultrapure water (UPW), and sucralose standard (purity: 99.9%) are required, and a content is determined by an external standard method.

Calculation Method of a Recovery Rate

A recovery rate in each example and comparative example is a mass percentage of an obtained sucralose solid product to a total content of sucralose in a sucralose reaction solution, wherein the total content of sucralose in the sucralose reaction solution could be determined by HPLC.

Example 1

A 250 mL three-necked round-bottomed flask with a mechanical stirring device was used. 80 g of a sucralose-containing concentrated reaction solution that had been treated by removing a solvent was added to the three-necked round-bottomed flask, and mL of ethyl acetate was added thereto to obtain a mixed solution. Stirring was started, and under stirring, the mixed solution was heated to 55° C. and stirred at 55° C. for 2 h, such that slurrying was completed, at which point a large amount of sucralose solid was precipitated in the three-necked flask. The resulting system was cooled to 5° C. at a cooling rate of 2° C./10 min, stirred at 5° C. for 1 h, and then filtered, and the resulting solid was collected, obtaining purified sucralose with an HPLC purity of 97% (which was calculated according to an HPLC peak area proportion) and a recovery rate of 85%.

Figure 4:
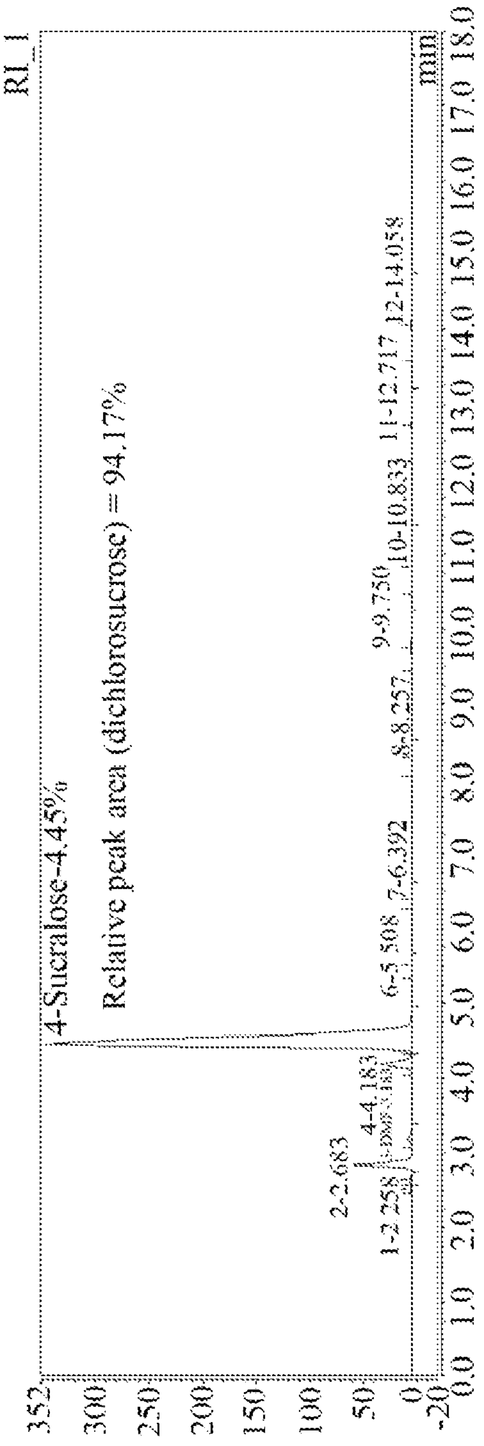
FIG. 4 shows an HPLC spectrum of a crude sucralose reaction solution.
Figure 5:
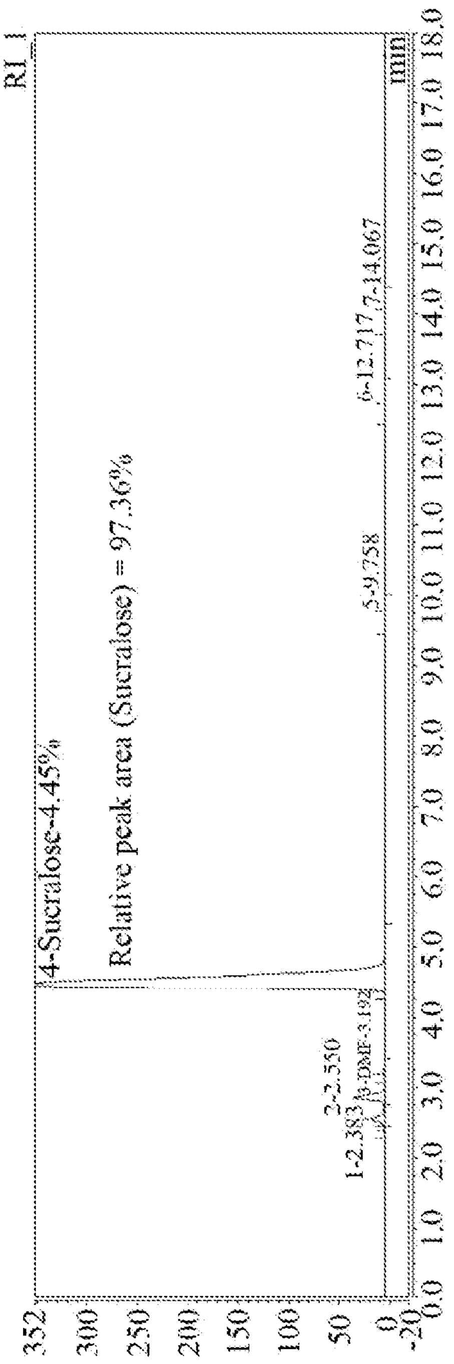
FIG. 5 shows an HPLC spectrum of sucralose obtained after the purification by the method according to Example 1.

FIG. 4 shows an HPLC spectrum of a crude sucralose reaction solution; and FIG. shows an HPLC spectrum of sucralose obtained after the treatment according to the method of Example 1. As shown in FIG. 4 and FIG. 5, the sucralose in FIG. 4 has an HPLC purity of about 94% (which is calculated according to an HPLC peak area proportion), and the sucralose in FIG. 5 has an HPLC purity of higher than 97% (97.36%, which was calculated according to an HPLC peak area proportion), indicating that the method of the present disclosure has a significant effect on the purification of sucralose.

Example 2

A 250 mL three-necked round-bottomed flask with a mechanical stirring device was used. 80 g of a sucralose-containing concentrated reaction solution that had been treated by removing a solvent was added to the three-necked round-bottomed flask, and mL of ethyl acetate was added thereto to obtain a mixed solution. Stirring was started, and under stirring, the mixed solution was heated to 60° C. and stirred at 60° C. for 1 h, at which point a large amount of sucralose solid was precipitated in a resulting system. The resulting system was cooled to 0° C. at a cooling rate of 3° C./10 min, stirred at 0° C. for 2 h, and then filtered, and the resulting solid was collected, obtaining purified sucralose with an HPLC purity of higher than 98% (which was calculated according to an HPLC peak area proportion) and a recovery rate of 78%.

Example 3

A 250 mL three-necked round-bottomed flask with a mechanical stirring device was used. 80 g of a sucralose-containing concentrated reaction solution that had been treated by removing a solvent was added to the three-necked round-bottomed flask, and mL of ethyl acetate was added thereto to obtain a mixed solution. Stirring was started, and under stirring, the mixed solution was heated to 50° C. and stirred at 50° C. for 3 h, at which point a large amount of sucralose solid was precipitated in a resulting system. The resulting system was cooled to 8° C. at a cooling rate of 1° C./10 min, stirred at 8° C. for 3 h, and then centrifuged, and a resulting solid was collected, obtaining purified sucralose with an HPLC purity of higher than 97% (which was calculated according to an HPLC peak area proportion) and a recovery rate of 82%.

Example 4

A 500 mL three-necked round-bottomed flask with a mechanical stirring device was used. 200 g of a sucralose-containing concentrated reaction solution that had been treated by removing a solvent was added to the three-necked round-bottomed flask, and mL of ethyl acetate was added thereto to obtain a mixed solution. Stirring was started, and under stirring, the mixed solution was heated to 60° C. and stirred at 60° C. for 3 h, at which point a large amount of sucralose solid was precipitated in a resulting system. The resulting system was cooled to 5° C. at a cooling rate of 1° C./10 min, stirred at 5° C. for 3 h, and then centrifuged, and a resulting solid was collected, obtaining purified sucralose with an HPLC purity of higher than 98% (which was calculated according to an HPLC peak area proportion) and a recovery rate of 85%.

Example 5 (Further Refining of a Sucralose Crystal)

100 g of the sucralose crystal obtained in Example 4 was taken and added to 100 mL of deionized water to obtain a first mixture. The first mixture was heated to 60° C. and stirred to completely dissolve the sucralose. 2 g of activated carbon was added thereto to obtain a second mixture. The second mixture was stirred at 60° C. for 1 h and then filtered while hot to remove the activated carbon and obtain a filtrate. The filtrate was collected and slowly cooled to 25° C. within 6 h, such that a large amount of sucralose crystal was precipitated in the resulting system. The resulting system was filtered, and a sucralose crystal was collected, obtaining refined sucralose with an HPLC purity of higher than 99% (which was calculated according to an HPLC peak area proportion) and a recovery rate of 70%.

Comparative Example 1

A 500 mL three-necked round-bottomed flask with a mechanical stirring device was used. 80 g of a sucralose-containing concentrated reaction solution that had been treated by removing a solvent was added to the three-necked round-bottomed flask, and 250 mL of water was added thereto for dissolution to obtain an aqueous solution. 200 mL of butyl acetate was added to the aqueous solution to obtain a mixed solution. Stirring was started, and the mixed solution was stirred at ambient temperature for 1 h to make butyl acetate fully extract impurities in the aqueous solution. A resulting system was left to stand and subjected to phase separation, obtaining an aqueous phase, in which sucralose had an HPLC purity of about 95% (which was calculated according to an HPLC peak area proportion) and a recovery rate of 90%.

It can be seen from the comparison between the examples and the comparative example that, compared with the impurity extraction process using butyl acetate widely used in the prior art, the purification method is provided in the present disclosure, in which a concentrate of a crude sucralose is the directly slurried without redissolving the crude sucralose in a solution. The purification method of the present disclosure has the advantages of simple operations, small treatment capacity, and small solvent consumption. In addition, ethyl acetate is a solvent widely used in the process to produce sucralose (such as chlorination), and the boiling point of ethyl acetate is much lower than the boiling point of butyl acetate, such that the energy consumption in the distillation for solvent recovery is greatly reduced, which is conducive to improving the production efficiency and reducing the production cost.

The above are merely preferred embodiments of the present disclosure, and are not intended to limit the present disclosure in any way. The methods and technical content disclosed above may be used by any person skilled in the art to make many possible variations and modifications to the technical solutions of the present disclosure or modify them into equivalent embodiments of equivalent variations, without departing from the scope of the technical solutions of the present disclosure. Therefore, any simple modifications, equivalent substitutions, equivalent changes, and modifications made to the above embodiments according to the technical essence of the present disclosure without departing from the content of the technical solutions of the present disclosure still fall within the protection scope of the technical solutions of the present disclosure.

What is claimed is:

1. A method for purifying sucralose, comprising:

removing a solvent from a sucralose reaction solution to obtain a concentrated crude sucralose solution;

under stirring, adding ethyl acetate into the concentrated crude sucralose solution, heating to a preset temperature, and holding at the preset temperature for a first preset time to obtain a crude product slurry containing sucralose crystal; and under stirring, subjecting the crude product slurry to gradient cooling to an endpoint temperature, holding at the endpoint temperature for a second preset time, and filtering to obtain the sucralose crystal; wherein the preset temperature is in a range of 45° C. to 65° C., the first preset time is in a range of 0.5 h to 3 h, the gradient cooling is conducted as follows: cooling the crude product slurry to the endpoint temperature at a cooling rate of 1° C./10 min to 3° C./10 min, and the endpoint temperature is in a range of 0° C. to 10° C., and the second preset time is in a range of 0.5 h to 3 h.

2. The method of claim 1, further comprising:

refining the sucralose crystal to further improve a purity of the sucralose crystal.

3. The method of claim 2, wherein the refining is conducted by recrystallization.

4. The method of claim 2, wherein the ethyl acetate is added in a volume of 0.2 mL to 0.5 mL per gram of the concentrated crude sucralose solution.

5. The method of claim 2, wherein, the solvent is removed by vacuum distillation or atmospheric distillation.

6. The method of claim 1, wherein the ethyl acetate is added in a volume of 0.2 mL to 0.5 mL per gram of the concentrated crude sucralose solution.

7. The method of claim 1, wherein the solvent is removed by vacuum distillation or atmospheric distillation.

* * * * *